United States Patent [19]
James

[11] Patent Number: 6,149,863
[45] Date of Patent: Nov. 21, 2000

[54] METHOD OF STEAM STERILIZATION USING A STEAM STERILIZATION INDICATOR

[75] Inventor: Phillip Richard James, Leicester, United Kingdom

[73] Assignee: Albert Browne Limited, United Kingdom

[21] Appl. No.: 09/394,384

[22] Filed: Sep. 10, 1999

Related U.S. Application Data

[62] Division of application No. 09/025,189, Feb. 18, 1998, abandoned.

[30] Foreign Application Priority Data

Feb. 19, 1997 [GB] United Kingdom .................. 9703468

[51] Int. Cl.$^7$ ........................................................ A61L 2/08
[52] U.S. Cl. ............................... 422/26; 422/56; 422/119; 436/1; 116/207
[58] Field of Search ................................ 422/26, 55, 56, 422/119; 436/1; 116/206, 207

[56] References Cited

U.S. PATENT DOCUMENTS

| | | |
|---|---|---|
| 2,195,395 | 4/1940 | Chapman . |
| 2,738,429 | 3/1956 | Goldblith . |
| 3,114,349 | 12/1963 | Schuman . |
| 4,015,937 | 4/1977 | Miyamoto et al. . |
| 4,155,895 | 5/1979 | Rohowetz . |
| 5,258,065 | 11/1993 | Fujisawa ............................. 106/22 B |
| 5,457,486 | 10/1995 | Malhotra et al. . |
| 5,486,459 | 1/1996 | Burnham et al. . |

OTHER PUBLICATIONS

"Electrochromic Fluid for Permanent Printing on Regular Paper Using Nonconsumable Electrodes. Apr. 1979," IBM Technical Disclosure Bulletin, 21(11):4722–4723 (1979).

*Primary Examiner*—Robert J. Warden, Sr.
*Attorney, Agent, or Firm*—Nixon Peabody LLP

[57] ABSTRACT

A steam-sensitive ink comprises, as active ingredient, a tetrazolium salt. The ink may be coated on, or impregnated into, a substrate to form a steam sterilization indicator.

21 Claims, No Drawings

METHOD OF STEAM STERILIZATION USING A STEAM STERILIZATION INDICATOR

This application is a division of U.S. patent application Ser. No. 09/025,189 filed Feb. 18, 1998, now abandoned, which claims priority of Great Britain Patent Application Serial No. GB9703468.0 filed Feb. 19, 1997.

This invention relates to indicator articles for use in steam sterilization processes, and to inks used in the preparation of such articles.

Pressurised steam is used in hospitals to sterilize reusable medical equipment. To differentiate between a tray containing sterilised goods and one containing non-sterile goods, which may not have been processed, an indicator is used. This is typically a strip of paper with a coloured mark printed on it. The process of sterilisation causes the mark on the strip to change colour. Often the original colour is light, and the colour after processing is dark. The change in colour is caused by a chemical reaction between the steam and the ink.

One of the most commonly used colour change indicators for sterilisation contains sulphur and lead salts. These compounds react under the conditions of steam sterilisation to produce lead sulphide, giving rise to a change in colour from yellow to black. Despite the widespread use and low cost of such indicators, there are several disadvantages associated with them. Firstly, the ink has a tendency to transfer to and stain articles with which it comes into contact in the autoclave. In addition to being unsightly, these stains may also contain highly toxic compounds which may be inadvertently administered to the patient. Secondly, the sensitivity of the ink diminishes with time, especially when stored in humid conditions, such that the initial and final colours may be compromised.

There are numerous other colour change systems capable of detecting steam sterilisation, containing metal salts, organic acids or other compounds. Many of these are not significantly less toxic than the lead/sulphur inks, have a limited colour change, and/or are expensive.

There has now been devised an indicator ink which overcomes or substantially mitigates the disadvantages associated with the prior art.

According to a first aspect of the present invention, a steam sensitive ink comprises, as active ingredient, a tetrazolium salt.

The tetrazolium salt used in the present invention will be a member of the class of compounds including the following general structure I:

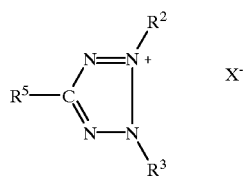

wherein X⁻ represents an anion, and at least one of $R^2$, $R^3$ and $R^5$, which may be same or different, represents an aromatic group.

Preferably, at least one, and more preferably both, of $R^2$ and $R^3$ represent aromatic groups. It is preferred that $R^5$ also represents an aromatic group.

Aromatic groups which $R^2$, $R^3$ and/or $R^5$ may represent include 5- and 6-membered monocyclic ring systems, both carbocyclic and heterocyclic, as well as fused ring systems. Examples include phenyl, naphthyl, quinolinyl, pyridyl and azolyl (eg oxazolyl, thiazolyl, benzoxazolyl, benzothiazolyl, etc). The rings may be unsubstituted, or may be substituted by one or more of a wide range of substituents. Examples of substituents which may be present are lower alkyl or lower alkoxy (ie alkyl or alkoxy with one to six carbon atoms, and which may be further substituted, eg with any of the substituents listed here), aryl groups (eg phenyl, benzyl, styryl, biphenyl, naphthyl etc), aryloxy (eg phenoxy), halogen (ie fluoride, chloride, bromide, iodide), nitro, amnino, cyanide, azide, etc.

Presently preferred aromatic groups which $R^2$, $R^3$ and/or $R^5$ may represent include unsubstituted or substituted monocyclic groups, most preferably phenyl and oxazolyl groups.

Particularly preferred compounds are those in which $R^3$ and $R^5$ both represent phenyl.

Where any of $R^2$, $R^3$ and $R^5$ does not represent an aromatic group, then it may represent hydrogen or an aliphatic group, eg a lower alkyl group, which may substituted with any of a wide range of substituents (eg those listed above).

Furthermore, one or more of the substituents $R^2$, $R^3$ and $R^5$ may act as a bridging group, connecting the tetrazolium ring to a further tetrazolium ring structure, ie the active ingredient may incorporate more than one such ring structure. For example, the active ingredient may have the general formula II:

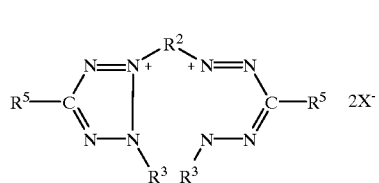

Preferred components include those in which $R^2$ acts as a bridge between two tetrazolium rings. In such a case, $R^2$ is most preferably a biphenyl group.

The counterion (X⁻) can be any anion, but is preferably chloride, bromide, iodide, tetrafluoroborate, hexafluorophosphate, perchlorate or sulphate.

Specific tetrazolium salts which may be mentioned include the following:

2,3,5-triphenyl-2H-tetrazoliun chloride 2-(p-iodophenyl)-3-(p-nitrophenyl)-5-phenyl-2H-tetrazolium chloride 3-(1-naphthyl)-2,5-diphenyl-2H-tetrazolium chloride 3-(4,5-dimethyl-2-thiazolyl)-2,5-diphenyl-2H-tetrazolium bromide 2-(2-benzothiazolyl)-3-(4-phthalhydrazidyl)-5-styryl-2H-tetrazoliurn chloride 3,3'-(3,3'-dimethoxy-4,4'-biphenylene)-bis-(2-(p-nitrophenyl)-5-(p-thiocarbamylphenyl)-2H-tetrazolium chloride)

3,3'-(4,4'-biphenylene)-bis-(2,5-diphenyl-2H-tetrazolium chloride)

3,3'-(3,3'-dimethoxy-4,4'-biphenylene)-bis-(2,5-diphenyl-2H-tetrazolium chloride)

3,3'-(3,3'-dimethoxy-4,4'-biphenylene)-bis-(2-(p-nitrophenyl)-5-phenyl-2H-tetrazolium chloride)

3,3'-(3,3'-dimethoxy-4,4'-biphenylene)-bis-(2,5-(p-nitrophenyl)-2H-tetrazolium chloride).

Numerous other tetrazolium salts are listed in U.S. Pat. No. 4,284,704.

The ink of the invention preferably also comprises a binder.

The binder may comprise any water resistant, heat resistant polymer. Suitable polymers include soluble polymers such as ethyl and nitro cellulose, cellulose acetate and its derivatives, hydroxypropyl cellulose, polystyrene, polymethacrylates, polyvinyl chloride, polyvinyl acetate; emulsion latexes such as polyvinylidene chloride, acrylics and polyvinyl acetate; cross-linking resins such as phenol-formaldehyde, urea-formaldehyde and melamine-formaldehyde; uv curing systems; and drying oils.

Presently preferred polymeric binders include cellulose derivatives, notably ethyl cellulose and nitrocellulose.

If required, a solvent may be used to provide a vehicle for the polymer. Suitable solvents for use in ink according to the invention are, for example, aliphatic alcohols, industrial methylated spirit, ethylene glycol alkyl ethers, eg ethylene glycol monoethylether, white spirit, aliphatic esters, eg isopropyl acetate, or aliphatic hydrocarbon solvents, or mixtures of two or more thereof. Water or aqueous solvent systems may also be suitable.

One particularly preferred solvent is 2-ethoxyethanol.

Further additives may be included to improve the coating process and the performance. Typical additives for improving coating include antifoaming agents and plasticisers. Performance can be enhanced by adding antioxidants which may be used to adjust the timing. Examples include ascorbic acid and hydroquinones. Polyhydroxybenzoic acids may be used to stabilise the system; these include the di- and tri-hydroxybenzoic acids. Addition of alkalis such as metal hydroxides, amines and guanidines may enhance the end colour and accelerate the colour change.

According to a second aspect of the invention, there is provided a steam sterilization indicator comprising an ink including, as active ingredient, a tetrazolium salt, coated on or impregnated in a substrate.

Substrates onto which the ink may be coated or impregnated include paper and similar materials which are permeable to steam but which maintain their integrity under steam sterilization conditions.

The ink and sterilization indicator according to the invention are advantageous primarily in that they undergo a distinct colour change when subjected to steam sterilization conditions. In addition, they may be less costly and/or less toxic than known materials, and/or may exhibit greater stability.

The invention will now be illustrated, by way of example only, with reference to the following Examples:

EXAMPLE 1

| | |
|---|---|
| Neotetrazolium chloride* | 7.5 g |
| 2,4-dihydroxybenzoic acid | 12.5 g |
| ethyl cellulose | 150 g |
| 2-ethoxyethanol | 1 l |
| diphenyl guanidine | 12.5 g |
| tannic acid | 7.5 g |

EXAMPLE 2

| | |
|---|---|
| Neotetrazolium chloride* | 7.5 g |
| 2,4-dihydroxybenzoic acid | 25 g |
| ethyl cellulose | 150 g |
| 2-ethoxy ethanol | 1 l |
| hydroquinone | 12.5 g |

EXAMPLE 3

| | |
|---|---|
| MTT** | 10 g |
| Ethanol | 1 l |
| Nitrocellulose | 400 g |
| Dibutyl phthalate | 5 g |

EXAMPLE 4

| | |
|---|---|
| Blue tetrazolium chloride*** | 10 g |
| 2 ethoxy ethanol | 1 l |
| ethyl cellulose | 150 g |
| 2,4,6 trihydroxybenzoic acid | 20 g |
| Ascorbic acid | 10 g |

EXAMPLE 5

| | |
|---|---|
| Nitroblue tetrazolium chloride**** | 13.5 g |
| Ethyl celluose | 168 g |
| 2-ethoxyethanol | 1 l |
| Hydroquinone | 2.2 g |
| 2,4-dihydroxy benzoic acid | 101 g |
| Tannic acid | 13.5 g |

* Neotetrazolium chloride = 3,3'-(4,4'-biphenylene)-bis-(2,5-diphenyl-2H-tetrazolium chloride)
** MTT = 3-(4,5-dimethyl-2-thiazolyl)-2,5-diphenyl-2H-tetrazolium chloride
*** Blue tetrazolium chloride = 3,3-(3,3'-dimethoxy-4,4'-biphenylene)-bis-(2,5-diphenyl-2H-tetrazolium chloride)
**** Nitroblue tetrazolium chloride = 3,3'-(3,3'-dimethoxy-4,4'-biphenylene)-bis-(2-(p-nitrophenyl)-5-phenyl-2H-tetaazolium chloride)

For each formulation, the components were mixed together and dissolved, then deposited on a paper substrate either by coating or printing.

What is claimed is:

1. A method of steam sterilization of an article comprising:

exposing to steam both said article and a steam sterilization indicator, said indicator comprising a tetrazolium salt that is reduced to a formazan compound or salt thereof and thereby undergoes a color change as a direct result of exposure to steam sterilization conditions.

2. A method as claimed in claim 1, wherein the tetrazolium salt is a member of the class of compounds including the general structure I:

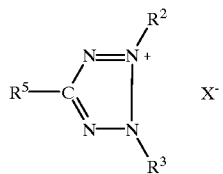

(I)

wherein X⁻ represents an anion, and at least one of R², R³ and R⁵, which may be same or different, represents an aromatic group.

3. A method as claimed in claim 2, wherein at least one of R² and R³ represents an aromatic group.

4. A method as claimed in claim 2, wherein each of R², R³ and R⁵ represents an aromatic group.

5. A method as claimed in claim 2, wherein the aromatic groups which R², R³ and/or R⁵ represent are selected from the group of 5- and 6-membered monocyclic ring systems, both carbocyclic and heterocyclic, and fused ring systems.

6. A method as claimed in claim 2, wherein the aromatic groups which R², R³ and/or R⁵ represent are selected from the group of phenyl, naphthyl, quinolinyl, pyridyl and azolyl.

7. A method as claimed in claim 2, wherein the aromatic groups which R², R³ and/or R⁵ represent are unsubstituted, or are substituted by one or more substituents selected from the group of lower alkyl, lower alkoxy, aryl groups, aryloxy, halogen, nitro, amino, cyanide, and azide.

8. A method as claimed in claim 2, wherein R², R³ and/or R⁵ represent phenyl or oxazolyl groups.

9. A method as claimed in claim 2, wherein R² and R³ both represent phenyl.

10. A method as claimed in claim 2, wherein X⁻ represents a counterion selected from the group of chloride, bromide, iodide, tetrafluoroborate, hexafluorophosphate, perchlorate and sulphate.

11. A method as claimed in claim 1, wherein the active ingredient is of the general formula II:

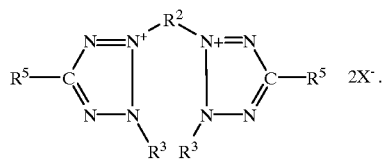

(II)

12. A method as claimed in claim 11, wherein R² is a biphenyl group.

13. A method as claimed in claim 1, wherein the tetrazolium salt is selected from the group of 2,3,5-triphenyl-2H-tetrazolium chloride;

2-(p-iodophenyl)-3-(nitrophenyl)-5-phenyl-2H-tetrazolium chloride;

3-(1-naphthyl)-2,5-diphenyl-2H-tetrazolium chloride;

3-(4,5-dimethyl-2-thiazolyl)-2,5-diphenyl-2H-tetrazolium bromide;

2-(2-benzothiazolyl)-3-(4-phthalhydrazidyl)-5-styryl-2H-tetrazolium chloride;

3,3'-(3,3'-dimethoxy-4,4'-biphenylene)-bis-(2-(p-nitrophenyl)-5-(p-thiocarbamylphenyl)-2H-tetrazolium chloride);

3,3'-(4,4'-biphenylene)-bis-(2,5-diphenyl-2H-tetrazolium chloride);

3,3'-(3,3'-dimethoxy-4,4'-biphenylene)-bis-(2,5-diphenyl-2H-tetrazolium chloride);

3,3'-(3,3'-dimethoxy-4,4'-biphenylene)-bis-(2-(p-nitrophenyl)-5-phenyl-2H-tetrazolium chloride); and 3,3'-(3,3'-dimethoxy-4,4'-biphenylene)-bis-(2,5-(p-nitrophenyl)-2H-tetrazolium chloride).

14. A method as claimed in claim 1, wherein said indicator further comprises a binder.

15. A method as claimed in claim 14, wherein the binder is selected from the group of ethyl and nitro cellulose, cellulose acetate and its derivatives, hydroxypropyl cellulose, polystyrene, polymethacrylates, polyvinyl chloride, polyvinyl acetate; emulsion latexes cross-linking resins; uv curing systems; and drying oils.

16. A method as claimed in claim 14, wherein the binder is a cellulose derivative.

17. A method as claimed in claim 1, wherein said indicator further comprises a solvent.

18. A method as claimed in claim 17, wherein the solvent is selected from the group of aliphatic alcohols, industrial methylated spirit, ethylene glycol alkyl ethers, white spirit, aliphatic esters, aliphatic hydrocarbon solvents, water, and mixtures of two or more thereof.

19. A method as claimed in claim 17, wherein the solvent is 2-ethoxyethanol.

20. A method as claimed in claim 1, wherein said tetrazolium salt is coated on or impregnated in a substrate.

21. A method as claimed in claim 20, wherein the substrate is a paper material which is permeable to steam but which maintains its integrity under steam sterilization conditions.

* * * * *